United States Patent [19]

Gilkerson et al.

[11] Patent Number: 4,921,524
[45] Date of Patent: May 1, 1990

[54] OXIMINO ETHER COMPOUNDS

[75] Inventors: Terence Gilkerson, Canterbury; Robert W. Shaw; David C. Jennens, both of Sittingbourne, all of England

[73] Assignee: Shell Internationale Research Maatschappij B.V., The Hague, Netherlands

[21] Appl. No.: 181,410

[22] Filed: Apr. 14, 1988

[30] Foreign Application Priority Data

May 15, 1987 [GB] United Kingdom ............... 8711525

[51] Int. Cl.$^5$ ............................................. A01N 43/30
[52] U.S. Cl. ............................................. 71/88; 71/98; 71/103; 71/105; 71/106; 71/118; 71/121; 560/250; 560/251; 558/412; 558/414; 549/442; 564/221; 564/256; 564/85; 564/86; 564/87
[58] Field of Search ............... 564/256, 221; 71/98, 71/88, 105, 106, 103, 111, 121, 118; 560/250, 251; 558/412, 414; 549/44 R

[56] References Cited

U.S. PATENT DOCUMENTS 3,989,737 11/1977 Sowaki et al. ............... 564/256
4,795,488 1/1989 Lee ................................. 71/98

FOREIGN PATENT DOCUMENTS

| 82694 | 6/1983 | European Pat. Off. | 71/98 |
| 85530 | 8/1983 | European Pat. Off. | 71/98 |
| 86588 | 8/1983 | European Pat. Off. | 71/98 |
| 0133349 | 2/1985 | European Pat. Off. | 564/256 |
| 218233 | 4/1987 | European Pat. Off. | 71/98 |
| 3329017 | 2/1985 | Fed. Rep. of Germany | 564/256 |
| 51-013756 | 2/1976 | Japan | 71/98 |
| 58-077848 | 5/1983 | Japan | 71/98 |
| 2137200 | 10/1984 | United Kingdom | 564/256 |
| 2141427 | 12/1984 | United Kingdom | 564/256 |

Primary Examiner—James H. Reamer

[57] ABSTRACT

The invention provides compounds of the general formula

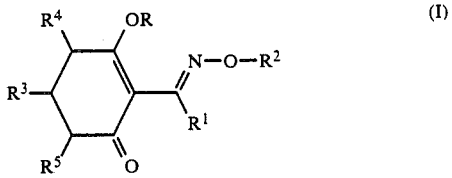

wherein
R represents a hydrogen atom, or an optionally substituted alkyl or acyl group, or an alkenyl or alkynyl group or an inorganic or organic cation;
$R^1$ represents an alkyl, haloalkyl, alkenyl, alkynyl or phenyl group;
$R^2$ represents an optionally substituted alkyl or phenalkyl group or a cycloalkyl, alkenyl, haloalkenyl, alkynyl or haloalkynyl group;
$R^3$ represents a hydrogen atom or an alkyl group; and one of $R_4$ and $R^5$ represents a hydrogen atom or an alkyl group, while the other of $R^4$ and $R^5$ represents an optionally substituted phenyl group; together with their use as herbicides and their preparation using novel intermediates.

9 Claims, No Drawings

OXIMINO ETHER COMPOUNDS

This invention relates to novel oximino ether compounds, to their use as herbicides, to their preparation, and to intermediates therefor, and their preparation.

In accordance with the present invention there are provided compounds of the general formula

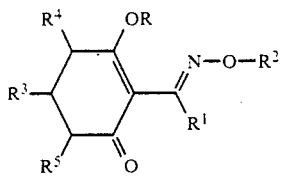

wherein
R represents a hydrogen atom, or an optionally substituted alkyl or acyl group, or an alkenyl or alkynyl group or an inorganic or organic cation;
$R^1$ represents an alkyl, haloalkyl, alkenyl, alkynyl or phenyl group;
$R^2$ represents an optionally substituted alkyl or phenalkyl group or a cycloalkyl, alkenyl, haloalkenyl, alkynyl or haloalkynyl group;
$R^3$ represents a hydrogen atom or an alkyl group;
one of $R^4$ and $R^5$ represents a hydrogen atom or an alkyl group, while the other of $R^4$ and $R^5$ represents an optionally substituted phenyl group.

In general terms it may be stated that, unless otherwise specified herein, a (halo)alkyl group, including the alkyl linkage of a phenalkyl group, suitably has 1-6, especially 1-4 carbon atoms; a (halo) alkenyl or alkynyl group has 2-6, especially 2-4 carbon atoms. Haloalkyl, haloalkenyl and haloalkynyl groups are suitably substituted by 1-3 halogen atoms. Fluorine and chlorine are the preferred halogen atoms. A cycloalkyl group preferably has 3-6 carbon atoms, and it most preferably cyclopropyl. An optionally substituted alkyl group may suitably be substituted by one or more moieties independently selected from halogen atoms and $C_{1-6}$ alkoxy, $C_{1-6}$ alkylthio, ($C_{1-6}$ alkoxy)carbonyl, and optionally substituted phenyl groups. An optionally substituted phenyl group may suitably be substituted by one or more moieties independently selected from halogen atoms and nitro, cyano, $C_{1-6}$ alkyl, $C_{1-6}$ haloalkyl, $C_{1-6}$ alkoxy, $C_{1-6}$ alkylthio, $C_{2-6}$ alkenylthio and alkynylthio, $C_{3-6}$ cycloalkylthio, benzylthio optionally substituted by 1-3 atoms of halogen, and $C_{1-6}$ alkyl, alkoxy, alkenyloxy, alkynyloxy and haloalkyl; and amino, acetmido, mono($C_{1-4}$) alkylamino and di($C_{1-4}$-alkyl)amino groups, and acyl groups. An acyl group may be defined as a group formed by removal of —OH from an organic acid. Suitable acyl groups include $C_{2-6}$ alkanoyl and optionally substituted benzoyl groups, and sulphonyl groups, for example alkylsulphonyl and optionally substituted phenylsulphonyl groups, and sulphonamido groups of formula $SO_2NQ^1Q^2$ where each of $Q^1$ and $Q^2$ independently represents a hydrogen atom or an alkyl group. Suitable as cations are alkali and alkaline earth metal ions, transition metal ions and optionally substituted ammonium ions, optional substituents being 1-4 groups independently selected from optionally substituted alkyl, phenyl and phenalkyl groups.

Preferably, R represents a hydrogen atom, or an organic or inorganic cation, or a $C_{2-6}$ alkanoyl group, especially acetyl, or an alkyl or arylsulphonyl group or a benzoyl group which is optionally substituted by 1-3 substituents independently selected from halogen, nitro, $C_{1-6}$ alkyl or $C_{1-6}$ alkoxy.

Most preferably, R represents a sodium, potassium or copper cation, or a tetraalkylammonium cation or an alkyl or arylsulphonyl group or an optionally substituted benzoyl group, or, especially, a hydrogen atom.

Preferably, $R^1$ represents a $C_{1-6}$ alkyl group, especially methyl, ethyl or n-propyl, or a phenyl group.

Preferably, $R^2$ represents a $C_{1-6}$ alkyl group optionally substituted by one or more moieties independently selected from halogen atoms and $C_{3-6}$ cycloalkyl, $C_{1-6}$ alkoxy carbonyl, $C_{1-6}$ alkoxy and $C_{1-6}$ alkylthio groups; or $C_{2-6}$ alkenyl, alkynyl, haloalkenyl, haloalkynyl or benzyl groups.

Most preferably $R^2$ represents $C_{1-4}$ alkyl or haloalkyl or $C_{2-4}$ alkenyl or haloalkenyl (especially allyl which is optionally substituted by a chlorine atom).

Preferably, $R^3$ independently represents hydrogen or $C_{1-4}$ alkyl, especially hydrogen or methyl.

Preferably, one of $R^4$ and $R^5$ represents a phenyl group optionally substituted by 1-5 moieties independently selected from halogen atoms and $C_{1-6}$ alkyl, $C_{2-6}$ alkenyloxy, cyano, nitro, acyl, $C_{1-6}$ haloalkyl, hydroxy, $C_{1-6}$ alkenyloxy and methylenedioxy groups, while the other of $R^4$ and $R^5$ represents a hydrogen atom or an alkyl group probably a hydrogen atom or $C_{1-4}$ alkyl, especially hydrogen or methyl.

It should be noted that when R is hydrogen the compounds of the invention may exist in any one of tautomeric forms as shown before:

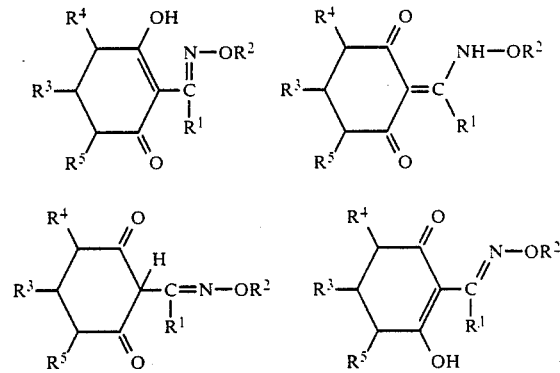

In this specification, recitation of any one of these forms denotes any tautomer or the tautomer mixture of which the recited form is a constituent. In relation to precursors, the reaction of any one tautomer also denotes any tautomer or the tautomer mixture.

The compounds of the invention may be prepared by a variety of methods and in a further aspect the invention provides methods for the preparation of compounds of formula I.

Conveniently the preparation of the compounds of the invention can be considered in three of four parts.

Part A involves the formation of a 4-(optionally substituted phenyl)cyclohexane-1,3-dione of formula II. This reaction is suitably carried out by reacting together compounds of formulae III and IV

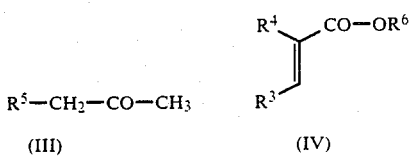

(III)     (IV)

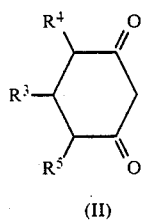

(II)

where $R^6$ represents an alkyl, preferably methyl or ethyl group, in the presence of an alkali metal alkoxide, for example sodium methoxide or ethoxide. The reaction suitably takes place in the presence of an inert organic solvent, for example benzene, toluene or xylene, at ambient or elevated temperature, for example 20°–150° C., preferably in the range 50° C. to the reflux temperature.

The starting materials III and IV are known or derivable from known compounds by standard methods.

Part B involves the acylation of a compound of formula II to give a 2-acyl-4-(optionally substituted phenyl)cyclohexane-1,3-dione of formula V

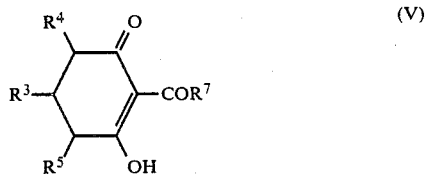

where $R^7$ represents an alkyl group. This may be effected by reacting a 4-(optionally substituted phenyl)-cyclohexane-1,3-dione of formula II with an acid $R^7$ COOH and/or a salt, anhydride or acid chloride thereof. The reaction suitably takes place in the presence of a polar organic solvent, for example pyridine or acetonitrile, at an elevated temperature, for example 40° C. to 150° C. in the presence of a Lesis acid, for example zinc chloride, zinc cyanide, aluminum chloride, 4-(N,N-dimethylamino)pyridine (DMAP), or a polymeric Lewis acid catalyst comprising at least one pyridylamino functional group, as described in AU No. 8652992.

Alternatively, the preferably, the acylation may be carried out by reacting a 4-(optionally substituted phenyl)cyclohexane-1,3-dione of formula II with an acid $R^7$ COOH and/or a salt, anhydride or acid halide thereof, in the presence of an amine base/solvent, suitably triethylamine or pyridine, to give an intermediate O-acyl derivative of formula VI

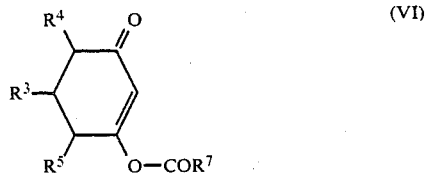

and then treating the intermediate of formula VI with $R^7$ COOH, or with imidazole, or with a Lewis acid, for example one of the reagents described above, such reactions suitably taking place in the presence of an organic solvent, for example a polar solvent such as pyridine or acetonitrile, or a hydrocarbon solvent, for example toluene or xylene, or a halogenated hydrocarbon, for example dichloromethane at a temperature in the range 20°–150° C.

Part C involves the formation of a compound of formula I wherein R is hydrogen. This reaction may be carried out by reacting a compound of formula V with hydroxylamine to give an intermediate oxime derivative of formula I wherein R represents hydrogen, and reacting said oxime derivative with a compound of formula $R^2$—L, wherein L is a leaving group such as, for example, chloride, bromide, iodide, sulphate, nitrate, methyl sulphate, ethyl sulphate, tetrafluoroborate, hexafluorophosphate, hexafluoroantimonate, methanesulphonate, fluorosulphonate, fluoromethanesulphonate and trifluoromethanesulphonate, or, preferably, by reacting a compound of formula V with a derivative of formula $H_2N$—O—$R^2$.

Oximination suitably takes place at a temperature in the range 0° to 50° C., conveniently at ambient temperature, optionally in the presence of water and/or an organic solvent, suitably an alcohol, for example methanol or ethanol, and optionally in the presence of a base, suitably an amine base such as triethylamine.

An optional step, Part D, involves the replacement of the hydrogen atom R with a substituent of the type defined above. Such replacement may occur in standard manner, by reaction with a suitable compound R—L, where L is a leaving group as defined above, or with an inorganic or organic base or salt, suitably at a temperature in the range 0°–100° C., preferably 20°–50° C., in the presence of an organic solvent and/or water.

A compound of formula V may be converted into another compound of formula V by substitution of the phenyl ring, for example by acylation, nitration or sulphonation, and/or by derivatisation using standard techniques.

Intermediate compounds of formulae V and VI are novel and therefore a further embodiment of the invention provides such novel compounds, and their preparation.

Compounds of formula I have been found to show interesting activity as herbicides, showing high activity against undesirable grasses, such as blackgrass, wild oats, annual meadow grass, Red Fescue and barnyard grass, whilst low or no activity against useful, non-tartget species, including linseed, mustard, sugar beet, rape and soya. Certain compounds of formula I have also been found to show selectivity to small grain cereals. Accordingly, the invention further provides a herbicidal, especially graminicidal, composition comprising a compound of formula I as defined above in association with at least one carrier, and a method of making such a composition, which comprises bringing a compound of formula I into association with at least one carrier.

The invention also provides the use of such a compound or composition according to the invention as a herbicide, especially as a graminicide. Further, in accordance with the invention there is provided a method of combating undesired plant growth at a locus by treating the locus with a compound or composition according to the invention. The locus may for example be a crop area in which the compound selectively combats weed growth. Application to the locus may be pre-emergence or post-energence. The dosage of active ingredient used may, for example, be from 0.01 to 10 kg/ha, preferably 0.05 to 4 kg/ha. A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example atapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydreocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide..

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10-50% w/v active ingredient, 2-20% w/v emulsifiers and 0-20% w/v of other additives such as stabilisers, penetrants and corrosion inhibitors. Suspension conentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing herbicidal, insecticidal or fungicidal properties. It is to be expected that certain mixture will give synergistic effects.

The invention will now be further described with reference to the accompanying Examples. Examples 1 to 78 relate to the preparation of precursors and the remaining Examples relate to the preparation of compounds of formula I. Structures of compounds were confirmed by mass spectrometry and nuclear magnetic resonance analysis.

EXAMPLE 1

Preparation of 4-(4-methoxyphenyl)cyclohexane-1,3-dione

A mixture of 4-methoxyphenylacetone (50 g) and methyl acrylate (26.2 g) was added dropwise to a stirred suspension of sodium methoxide (from 7.5 g sodium in 50 ml methanol) in dry xylene (160 ml) at ambient temperature. The resulting solution was then refluxed for 3 hours. The xylene was evaporated in vacuo and the residue partitioned between water and diethyl ether. The aqueous phase was further extracted with diethyl ether. The aqueous layer was finally acidified with concentrated hydrochloric acid to precipitate 4-(4-methoxyphenyl)cyclohexane-1,3-dione (37 g) as a white solid (after an ether washing) of m.p. 150°–151° C.

Theory for $C_{13}H_{14}O_3$: C 71.5; H 6.4%. Found: C 70.7; H 6.4%.

The following precursor compounds of formula III, set out in Table I, were prepared in the manner of the compound of the previous Example.

TABLE I

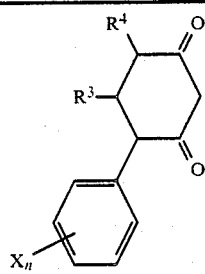

(III)

| Example No | $X^n$ | $R^3$ | $R^4$ | Analysis C Cal. % | C Fd. % | H Cal. % | H Fd. % | m.p. (°C.) |
|---|---|---|---|---|---|---|---|---|
| 2 | H | H | H | 76.6 | 76.1 | 6.4 | 6.4 | 110–112 |
| 3 | 4-Cl | H | H | 64.9 | 64.7 | 5.0 | 5.1 | 140–142 |
| 4 | 2-Cl | H | H | 64.9 | 64.5 | 5.0 | 5.1 | 145–147 |
| 5 | 2-MeO | H | H | 71.5 | 69.6 | 6.4 | 6.5 | 68–70 |
| 6 | 4-Me | H | H | 77.2 | 77.3 | 6.9 | 7.0 | 157–159 |
| 7 | 2-Me | H | H | 77.2 | 73.8 | 6.9 | 6.7 | 39–40 |
| 8 | H | H | Me | 77.2 | 76.2 | 6.9 | 6.5 | 41–42 |
| 9 | 4-OMe | Me | H | 72.4 | 72.2 | 6.9 | 6.9 | 118–119 |
| 10 | 4-Me | Me | H | 77.7 | 76.6 | 7.4 | 7.5 | 141–142 |
| 11 | 2,5-di-Me | H | H | 77.7 | 76.6 | 7.4 | 7.5 | 141–142 |
| 12 | 3,4-di-Me | H | H | 77.7 | 77.9 | 7.4 | 7.4 | oil |
| 13 | 2,4-di-Me | H | H | 77.7 | 72.0 | 7.4 | 7.5 | 145–146 |
| 14 | 4-F | H | H | 69.9 | 70.6 | 5.3 | 5.7 | 131–133 |
| 15 | 3,4-methylenedioxy | H | H | 67.2 | 67.2 | 5.2 | 5.1 | 130–132 |
| 16 | 3-MeO | H | H | 71.6 | 71.6 | 6.4 | 6.5 | 115–117 |
| 17 | 3-CF$_3$ | H | H | 60.9 | 59.7 | 4.3 | 4.3 | 176–178 |
| 18 | 3,4-di-MeO | H | H | 67.7 | 67.5 | 6.5 | 6.4 | 126–129 |
| 19 | 3-Cl | H | H | 64.7 | 65.0 | 4.9 | 5.1 | oil |
| 20 | 3-Me | H | H | 77.2 | 76.5 | 6.9 | 6.6 | 101–102 |
| 21 | 3-CH$_2$=CH—CH$_2$—O | H | H | 73.8 | 71.8 | 6.6 | 6.9 | oil |
| 22 | 3-nBuO | H | H | 73.8 | 68.3 | 7.7 | 7.9 | oil |
| 23 | 2-F | H | H | 69.9 | 68.5 | 5.3 | 5.4 | 157–160 |
| 24 | 3-EtO | H | H | 72.4 | 70.0 | 6.9 | 7.2 | 87–91 |
| 25 | 3-nPrO | H | H | 73.2 | 69.0 | 7.3 | 7.0 | oil |
| 26 | 3-HO | H | H | 70.6 | 69.7 | 5.9 | 5.4 | oil |
| 27 | 4-CN | H | H | 73.2 | 72.7 | 5.2 | 5.1 | 163–165 |

EXAMPLE 28

Preparation of 2-butyryl-3-hydroxy-4-(4-methoxyphenyl)cyclohex-2-ene-1-one

Triethylamine (11.1 g) was added dropwise to a stirred solution of 4-(4-methoxyphenyl)cyclohexane-1,3-dione (21.8 g) and n-butyryl chloride (17.6 g) in methylene chloride (100 ml) at ambient temperature. After stirring for a further 1 hour, the reaction solution was washed with water, brine and dried over anhydrous magnesium sulphate. The methylene chloride was removed in vacuo to give a mixture of 4-(4-methoxyphenyl)-1-butyryloxycyclohex-1-en-3-one and 6-(4-methoxyphenyl)-1-butyryloxycyclohex-1-ene-3-one.

Toluene (150 ml) was added followed by 4-(N,N-dimethylamino) pyridine (0.5 g) and the mixture refluxed for 8 hours. Evaporation of the toluene in vacuo gave a red oil. Purification on a silica gel column using 5% v/v diethyl ether-methylene chloride as eluant gave the title compound (25 g) as an orange oil.

Mass spectrometry: m/e found 288.

Theory for $C_{17}H_{20}O_4$; C 70.8; H 6.9%. Found: C 70.6; H 6.8%.

EXAMPLE 29

Preparation of 2-acetyl-3-hydroxy-4-(4-fluorophenyl)cyclohex-2-ene-1-one

A solution of 4-(4-fluorophenyl)cyclohexane-1,3-dione (4 g), acetic anhydride (6 ml) and 4-(N,N-dimethylamino) pyridine (0.2 g) in toluene (50 ml) was refluxed 3 hours. Evaporation of the toluene in vacuo gave a red oil, which, after purification on a silica gel column using 5% (v/v) diethyl ether-methylene chloride as eluant, gave the title compound as a yeoolw solid (4 g) of m.p. 67°–68° C.

Mass spectrometry: m/e found 248.
Theory for $C_{14}H_{13}O_3F$: C 67.7; H 5.2%. Found: C 67.8; H 5.4%.

EXAMPLE 30

Preparation of 2-butyryl-3-hydroxy-4-phenyl-cyclohex-2-ene-1-one

Zinc chloride (7.1 g) was added to pyridine (50 ml) followed by 4-phenylcyclohexane-1,3-dione (5 g). n-Butyryl chloride (2.6 g) was then added dropwise and the mixture heated to reflux for 4 hours. After cooling, the mixture was poured into 5N hydrochloric acid (200 ml) and the aqueous phase extracted with methylene chloride. The extracts were dried over magnesium sulphate, filtered and evaporated to give a red oil. Purification on a silica gel column using methylene chloride as eluent gave the title compound as an orange oil (2.15 g).

Mass spectrometry: m/e found 258
Theory for $C_{16}H_{18}O_3$: C 74.4; H 7.0%. Found: C 74.3; H 7.1%.

EXAMPLE 31

Preparation of 3-hydroxy-2-propionyl-4-(4-methyl-3-nitrophenyl)cyclohex-2-ene-1-one 3-hydroxy-2-propionyl-4-(4-methylphenyl)cyclohex-2-ene-1-one (1.2 g) in acetic anhydride (3 g) was cooled to 5° C. A solution of fuming nitric acid (0.42 g) in glacial acetic acid (0.3 g) and acetic anhydride (0.3 g) was added dropwise over a period of 5 minutes. After stirring for a further 1 hour at 5° C. and 2 hours at room temperature, the mixture was poured onto ice-water (100 ml). The aqueous solution was extracted with diethyl ether. The extracts were washed with aqueous sodium bicarbonate, dried over magnesium sulphate, filtered and the ether evaporated in vacouo. The residue was purified on a silica gel column using chloroform as eluant to give the title compound (0.5 g) as a yellow oil.

Mass spectrometry: m/e found 303.
Theory for $C_{16}H_{17}NO_5$: C 63.4; N 4.6%. Found: C 62.9; H 5.4; N 4.3%.

EXAMPLE 32

Preparation of 3-hydroxy-2-propionyl-4-(3-N,N-dimethylsulphonamido-4-methyphenyl)cyclohex-2-ene-1-one Chlorosulphonic acid (20 ml) was added dropwise to an ice-cold solution of 3-hydroxy-2-propionyl-4-(4-methylphenyl)cyclohex-2-ene-1-one (3.25 g) in chloroform (40 ml). After stirring at room temperature for 4 hours, the mixture was carefully poured onto ice. The chloroform layer was separated and the aqueous phase extracted with more chloroform. The combined extracts were dried over magnesium sulphate, filtered and the chloroform evaporated in vacuo to give 3-hydroxy-2-propionyl-4-(3-chlorosulphonyl-4-methylphenyl)cyclohex-2-ene-1-one (4.4 g). Water (50 ml) was added to the latter, followed by dimethylamine (2 g) and the solution stirred at room temperature for ½ hour. The solution was acidified with dilute hydrochloric acid. and extracted with dichloromethane. After drying over magnesium sulphate, the dichloromethane was evaporated in vacuo to give a pale yellow oil. Purification on a silica gel column using chloroform as eluant gave the title compound (4.0 g) as a white solid of m.p. 95°–97° C.

Mass spectrometry: m/e found 365.
Theory for $C_{18}H_{23}NO_5S$: C 59.2; H 6.3; N 3.8%. Found: C 59.0; H 6.5; N 3.8%.

EXAMPLE 33

Preparation of 2-butyryl-3-hydroxy-4-(3-acetyl-4-hydroxyphenyl)cyclohex-2-ene-1-one 2-Butyryl-3-hydroxy-4-(4-methoxyphenyl)cyclohex-2-ene-1-one (7.1 g) in dichloroethane (35 ml) was added to a suspension of aluminium chloride (10.5 g) in dichloroethane (50 ml) at 0° C. After stirring for ½ hour, a solution of acetyl chloride (2.2 g) in dichloroethane (25 ml) was added dropwise. After stirring a further ½ hour at 0° C., the reaction mixture was allowed to come to room temperature and poured into cold 5N hydrochloric acid (50 ml). The aqueous solution was then extracted with dichloromethane. The extracts were dried over magnesium sulphate and evaporated in vacuo to give a red oil. Purification on a silica gel column using 5% (v/v) diethylether-dichloromethane as eluant gave the title compound (1.3 g) as a clear oil.

Mass spectrometry: m/e found 316.
Theory for $C_{18}H_{20}O_5$: C 68.3; H 6.3%. Found: C 67.8; H 6.5%.

The following precursor compounds of formula II, set out in Table II, were made in a manner analogous to Examples 28 to 33.

TABLE II

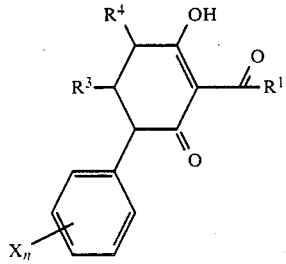

(II)

| Example No. | $X_n$ | $R^1$ | $R^3$ | $R^4$ | C Calc. % | C Fd. % | H Calc. % | H Fd. % | N Calc. % | N Fd. % | m.p.(°C.)/oil |
|---|---|---|---|---|---|---|---|---|---|---|---|
| 34 | H | Et | H | H | 73.8 | 73.8 | 6.6 | 6.5 | | | 68–70 |
| 35 | 4-Cl | "Pr | H | H | 65.6 | 65.8 | 5.8 | 6.0 | | | yellow oil |
| 36 | 2-Cl | "Pr | H | H | 65.6 | 65.5 | 5.8 | 5.9 | | | yellow oil |
| 37 | 4-Cl | Et | H | H | 64.6 | 64.2 | 5.4 | 5.5 | | | yellow oil |

TABLE II-continued

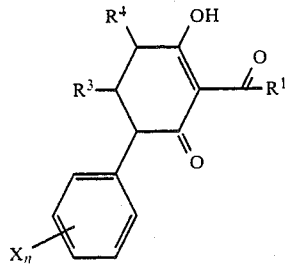

(II)

| Example No. | $X_n$ | $R^1$ | $R^3$ | $R^4$ | Analysis C Calc. % | Fd. % | H Calc. % | Fd. % | N Calc. % | Fd. % | m.p.(°C.)/oil |
|---|---|---|---|---|---|---|---|---|---|---|---|
| 38 | 2-Cl | Et | H | H | 64.6 | 64.3 | 5.4 | 5.4 | | | 90–92 |
| 39 | 2-Me | nPr | H | H | 75.0 | 73.9 | 7.4 | 7.4 | | | 37–38 |
| 40 | 4-Me | nPr | H | H | 75.0 | 73.9 | 7.4 | 7.4 | | | yellow oil |
| 41 | 2-Me | Et | H | H | 74.4 | 74.6 | 6.9 | 6.9 | | | oil |
| 42 | 4-Me | Et | H | H | 74.4 | 73.6 | 6.9 | 6.8 | | | oil |
| 43 | H | nPr | H | Me | 75.0 | 74.5 | 7.4 | 7.4 | | | yellow oil |
| 44 | 4-MeO | Et | Me | H | 70.8 | 68.4 | 6.9 | 6.8 | | | yellow oil |
| 45 | 4-Me | nPr | Me | H | 75.5 | 75.7 | 7.7 | 7.8 | | | yellow oil |
| 46 | 4-Me | Et | Me | H | 75.0 | 73.6 | 7.3 | 7.3 | | | yellow oil |
| 47 | 2-OMe | Et | H | H | 70.1 | 71.1 | 6.6 | 6.6 | | | 104–106 |
| 48 | 2,5-di-Me | Et | H | H | 75.0 | 74.9 | 7.3 | 7.5 | | | 109–110 |
| 49 | 2,5-di-Me | nPr | H | H | 75.5 | 75.1 | 7.7 | 8.0 | | | 78–80 |
| 50 | 3,4-di-Me | Et | H | H | 75.0 | 75.2 | 7.3 | 7.3 | | | 113–115 |
| 51 | 3,4-di-Me | nPr | H | H | 75.5 | 75.6 | 7.7 | 7.8 | | | 40–42 |
| 52 | 2,4-di-Me | Et | H | H | 75.0 | 74.6 | 7.4 | 7.4 | | | 40–41 |
| 53 | 2,4-di-Me | nPr | H | H | 75.7 | 75.8 | 7.7 | 7.8 | | | oil |
| 54 | 4-F | Et | H | H | 68.7 | 69.6 | 5.7 | 5.9 | | | oil |
| 55 | 4-F | nPr | H | H | 69.5 | 69.3 | 6.1 | 6.1 | | | oil |
| 56 | 3,4-methylenedioxy | Me | H | H | 65.7 | 65.6 | 5.1 | 5.1 | | | 98–99 |
| 57 | 3,4-methylenedioxy | Et | H | H | 66.6 | 66.7 | 5.5 | 5.5 | | | 100–101 |
| 58 | 3,4-methylenedioxy | nPr | H | H | 67.5 | 65.9 | 5.9 | 5.8 | | | oil |
| 59 | 3-MeO— | Et | H | H | 70.0 | 69.4 | 5.6 | 6.6 | | | oil |
| 60 | 3-MeO— | Me | H | H | 69.2 | 68.2 | 6.1 | 6.1 | | | oil |
| 61 | 4-SO$_2$NHEt | Et | H | H | 58.1 | 59.7 | 6.0 | 6.3 | 4.0 | 4.5 | oil |
| 62 | 4-SO$_2$NMe$_2$ | Et | H | H | 58.1 | 59.7 | 6.0 | 6.3 | 4.0 | 4.5 | oil |
| 63 | 2-MeO | nPr | H | H | 70.8 | 69.3 | 6.9 | 7.0 | | | 67–69 |
| 64 | 3-CF$_3$ | nPr | H | H | 62.6 | 62.7 | 5.2 | 5.6 | | | oil |
| 65 | 3-CF$_3$ | Et | H | H | 61.5 | 61.4 | 4.8 | 4.8 | | | oil |
| 66 | 3,4-di-MeO | Et | H | H | 67.1 | 67.0 | 6.6 | 6.5 | | | oil |
| 67 | 3,4-di-MeO | nPr | H | H | 67.9 | 67.5 | 6.9 | 6.8 | | | oil |
| 68 | 3-Cl | Et | H | H | 64.6 | 63.8 | 5.4 | 5.5 | | | oil |
| 69 | 3-Me | Et | H | H | 74.4 | 74.0 | 6.9 | 7.1 | | | oil |
| 70 | 3-CH$_2$=CH.CH$_2$O | Et | H | H | 72.0 | 73.4 | 6.7 | 6.9 | | | oil |
| 71 | 3-nBuO— | Et | H | H | 72.2 | 72.2 | 7.6 | 7.5 | | | oil |
| 72 | 2-F | Et | H | H | 68.7 | 68.6 | 5.7 | 5.9 | | | 77–81 |
| 73 | 3-EtO | Et | H | H | 70.8 | 70.3 | 6.9 | 6.9 | | | oil |
| 74 | 3-nPrO | Et | H | H | 71.5 | 66.8 | 7.3 | 7.0 | | | oil |
| 75 | 3-HO | Et | H | H | 69.2 | 68.0 | 6.2 | 6.9 | | | oil |
| 76 | 4-CN | Et | H | H | 71.4 | 71.4 | 5.6 | 5.6 | | | 90–91 |
| 77 | H | Ph | H | H | 78.1 | 74.7 | 5.5 | 6.0 | | | oil |
| 78 | 3-n-PrO | nPr | H | H | 72.2 | 70.4 | 7.6 | 7.5 | | | oil |

EXAMPLE 79

Preparation of 2-[1-(allyloxyimino)-n-butyl]-3-hydroxy-4-(4-methoxyphenyl)-cyclohex-2-en-1-one Triethylamine (1.2 g) was added to a solution of 2-butyryl-3-hydroxy-4-(4-methoxyphenyl)cyclohex-2-en-1-one (2.9 g) and O-allylhydroxylamine hydrochloride (1.2 g) in absolute ethanol (50 ml) at ambient temperature. After stirring overnight at this temperature, the ethanol was evaporated in vacuo, water was added to the residue and the aqueous solution was extracted with methylene chloride. The organic extracts were dried over anhydrous magnesium sulphate and then evaporated in vacuo. The residue was chromatographed on a silica gel column using 10% Et$_2$O—CH$_2$Cl$_2$ as eluant to give the title compound (2.3 g) as a yellow oil.

Mass spectrometry: m/e found 343; calculated 343.

Theory for C$_{20}$H$_{25}$HO$_4$: C 69.9; H 7.3; N 4.1%. Found: C 70.6; H 7.4; N 4.2%.

The folowing compounds of formula I, set out in Table III below, were prepared as described hereinbefore, in particular as described in the previous Example.

TABLE III

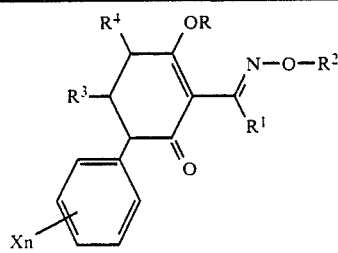
(I)

| Example No. | Xn | R | R¹ | R² | R³ | R⁴ | C Calc. % | C Fd. % | H Calc. % | H Fd. % | N Calc. % | N Fd. % | M/e (Calc/found) or mp(°C.) |
|---|---|---|---|---|---|---|---|---|---|---|---|---|---|
| 80 | 4-Me | H | Et | allyl | H | H | 72.8 | 73.2 | 7.3 | 7.3 | 4.5 | 4.5 | 313/313 |
| 81 | 4-Me | H | Et | Et | H | H | 71.7 | 70.0 | 7.6 | 7.4 | 4.6 | 4.8 | 301/301 |
| 82 | 2-Me | H | Et | allyl | H | H | 72.8 | 72.8 | 7.3 | 7.3 | 4.5 | 4.6 | 313/313 |
| 83 | 2-Me | H | Et | Et | H | H | 71.7 | 72.1 | 7.6 | 7.6 | 4.6 | 4.9 | 301/301 |
| 84 | 4-Me | H | ⁿPr | Et | H | H | 72.3 | 70.8 | 7.9 | 7.9 | 4.4 | 4.5 | 315/315 |
| 85 | 4-Me | H | ⁿPr | allyl | H | H | 73.3 | 73.7 | 7.6 | 7.6 | 4.3 | 4.4 | 327/327 |
| 86 | 2-Me | H | ⁿPr | Et | H | H | 72.3 | 72.2 | 7.9 | 7.9 | 4.4 | 4.8 | 315/315 |
| 87 | 2-Me | H | ⁿPr | allyl | H | H | 73.3 | 74.0 | 7.6 | 7.7 | 4.3 | 4.5 | 327/327 |
| 88 | H | H | ⁿPr | allyl | H | H | 72.8 | 73.0 | 7.3 | 7.6 | 4.5 | 4.8 | 313/313 |
| 89 | H | H | ⁿPr | Et | H | H | 71.8 | 71.1 | 7.6 | 7.5 | 4.7 | 5.0 | 301/301 |
| 90 | H | H | Et | allyl | H | H | 72.2 | 72.7 | 7.0 | 7.1 | 4.7 | 5.0 | 299/299 |
| 91 | H | H | Et | Et | H | H | 71.1 | 70.7 | 7.3 | 7.4 | 4.9 | 4.8 | 287/287 |
| 92 | 4-Cl | H | ⁿPr | allyl | H | H | 65.6 | 65.3 | 6.3 | 6.6 | 4.0 | 3.9 | 347/347 |
| 93 | 2-Cl | H | ⁿPr | Et | H | H | 64.4 | 64.3 | 6.6 | 6.7 | 4.2 | 4.5 | 335/335 |
| 94 | 2-Cl | H | ⁿPr | allyl | H | H | 65.6 | 65.4 | 6.3 | 6.4 | 4.0 | 4.1 | 347/347 |
| 95 | 4-Cl | H | Et | Et | H | H | 63.4 | 63.6 | 6.2 | 6.3 | 4.4 | 3.9 | 321/321 |
| 96 | 4-Cl | H | Et | allyl | H | H | 64.7 | 65.0 | 6.0 | 6.2 | 4.2 | 4.3 | 333/333 |
| 97 | 2-Cl | H | Et | Et | H | H | 63.4 | 63.3 | 6.2 | 6.2 | 4.4 | 3.73 | 321/321 |
| 98 | H | H | ⁿPr | allyl | H | Me | 73.4 | 73.3 | 7.6 | 8.0 | 4.3 | 4.2 | 327/327 |
| 99 | 4-OMe | H | ⁿPr | Et | H | H | 68.8 | 68.7 | 7.5 | 8.1 | 4.2 | 4.1 | 331/331 |
| 100 | 4-OMe | H | Et | allyl | Me | H | 70.0 | 69.2 | 7.3 | 7.1 | 4.1 | 4.5 | 343/343 |
| 101 | 4-OMe | H | Et | Et | Me | H | 68.9 | 68.6 | 7.5 | 7.0 | 4.2 | 4.4 | 331/331 |
| 102 | 4-Me | H | Et | Et | Me | H | 72.4 | 71.0 | 7.9 | 7.8 | 4.4 | 4.7 | 315/315 |
| 103 | 4-Me | H | Et | allyl | Me | H | 73.4 | 73.4 | 7.6 | 7.6 | 4.3 | 4.4 | 327/327 |
| 104 | 4-Me | H | ⁿPr | Et | Me | H | 73.0 | 72.5 | 8.2 | 8.2 | 4.3 | 4.2 | 329/329 |
| 105 | 4-Me | H | ⁿPr | allyl | Me | H | 74.0 | 73.3 | 7.9 | 8.1 | 4.1 | 4.3 | 341/341 |
| 106 | 4-OMe | H | ⁿPr | benzyl | H | H | 73.3 | 72.9 | 6.9 | 6.9 | 3.6 | 3.6 | 393/393 |
| 107 | 2-Cl | H | Et | allyl | H | H | 64.7 | 64.7 | 6.0 | 6.0 | 4.2 | 4.3 | 333/333 |
| 108 | 2-OMe | H | Et | Et | H | H | 68.1 | 68.6 | 7.3 | 7.4 | 4.4 | 5.0 | 317/317 |
| 109 | 2-OMe | H | Et | allyl | H | H | 69.3 | 69.6 | 7.6 | 7.3 | 4.3 | 4.4 | 329/329 |
| 110 | 2-OMe | K | Et | Et | H | H | 60.8 | 57.2 | 6.2 | 5.9 | 3.9 | 4.2 | 262-265 |
| 111 | 2,5-di-Me | H | ⁿPr | Et | H | H | 73.0 | 72.5 | 8.2 | 9.1 | 4.2 | 4.2 | 329/329 |
| 112 | 2,5-di-Me | H | ⁿPr | allyl | H | H | 74.0 | 74.0 | 7.9 | 7.9 | 4.1 | 4.3 | 341/341 |
| 113 | 2,4-di-Me | H | Et | Et | H | H | 72.4 | 71.7 | 7.9 | 7.9 | 4.4 | 4.6 | 315/315 |
| 114 | 2,5-di-Me | H | Et | allyl | H | H | 73.4 | 71.7 | 7.6 | 7.6 | 4.3 | 4.5 | 327/327 |
| 115 | 3,4-di-Me | H | ⁿPr | Et | H | H | 72.9 | 71.5 | 8.2 | 8.0 | 4.3 | 4.3 | 329/329 |
| 116 | 3,4-di-Me | H | Et | allyl | H | H | 73.4 | 69.9 | 7.6 | 7.5 | 4.3 | 4.2 | 327/327 |
| 117 | 3,4-di-Me | H | Et | Et | H | H | 72.4 | 72.6 | 7.9 | 8.2 | 4.4 | 4.3 | 315/315 |
| 118 | 2,4-di-Me | H | ⁿPr | Et | H | H | 72.9 | 71.8 | 8.2 | 8.1 | 4.3 | 4.3 | 329/329 |
| 119 | 2,4-di-Me | H | Et | Et | H | H | 72.4 | 72.0 | 7.9 | 7.9 | 4.4 | 4.6 | 315/315 |
| 120 | 2,4-di-Me | H | Et | allyl | H | H | 73.4 | 72.8 | 7.6 | 7.6 | 4.3 | 4.3 | 327/327 |
| 121 | 2,4-di-Me | H | ⁿPr | allyl | H | H | 73.9 | 72.8 | 7.9 | 7.9 | 4.1 | 3.9 | 341/341 |
| 122 | 3-NO₂, 4-Me | H | Et | Et | H | H | 62.4 | 62.7 | 6.4 | 6.6 | 8.1 | 8.1 | 96-99 |
| 123 | 2-MeO | H | ⁿPr | allyl | H | H | 70.0 | 70.1 | 7.9 | 70.6 | 4.1 | 4.1 | 343/343 |
| 124 | 3-CF₃ | H | ⁿPr | Et | H | H | 61.8 | 61.7 | 6.0 | 6.1 | 3.8 | 3.7 | 369/369 |
| 125 | 3-CF₃ | H | ⁿPr | allyl | H | H | 63.0 | 62.7 | 5.8 | 5.8 | 3.7 | 3.6 | 381/381 |
| 126 | 3-CF₃ | H | Et | Et | H | H | 60.8 | 61.2 | 5.6 | 5.5 | 3.9 | 3.9 | 355/355 |
| 127 | 3-CF₃ | H | Et | allyl | H | H | 62.1 | 61.6 | 5.4 | 5.2 | 3.8 | 3.8 | 367/367 |
| 128 | 3-CF₃ | -C(=O)-(2,4-Cl₂-C₆H₃) | Et | allyl | H | H | 57.8 | 57.7 | 4.1 | 4.1 | 2.6 | 2.6 | 540/540 |
| 129 | 2-MeO | -C(=O)-(4-Cl-C₆H₄) | Et | allyl | H | H | 66.7 | 66.5 | 5.6 | 5.6 | 3.0 | 3.7 | 467/467 |
| 130 | 2-Cl | H | ⁿPr | -CH₂-C₆H₅ | H | H | 69.4 | 69.4 | 6.0 | 6.2 | 3.5 | 4.0 | 397/397 |

TABLE III-continued (I structure shown: cyclohexenone with R⁴, OR, R³, Xn-phenyl, =N-O-R², R¹)

| Example No. | Xn | R | R¹ | R² | R³ | R⁴ | C Calc. % | C Fd. % | H Calc. % | H Fd. % | N Calc. % | N Fd. % | M/e (Calc/found) or mp(°C.) |
|---|---|---|---|---|---|---|---|---|---|---|---|---|---|
| 131 | 2-MeO | H | Et | —CH₂—Ph | H | H | 72.8 | 72.7 | 6.6 | 6.9 | 3.7 | 3.8 | 379/379 |
| 132 | 3-CF₃ | H | nPr | —CH₂—cyclopropyl | H | H | 63.8 | 62.4 | 6.1 | 6.0 | 3.5 | 3.6 | 395/395 |
| 133 | 2-Cl | H | Et | —CH₂—cyclopropyl | H | H | 65.6 | 65.2 | 6.3 | 6.3 | 4.0 | 3.9 | 347/347 |
| 134 | 2-MeO | H | Et | —CH₂—cyclopropyl | H | H | 70.0 | 70.0 | 7.3 | 7.5 | 4.1 | 4.0 | 343/343 |
| 135 | 3-MeCO, 4-OH | H | nPr | allyl | H | H | 67.9 | 67.5 | 6.7 | 6.8 | 3.8 | 4.1 | 371/371 |
| 136 | 3-SO₂NMe₂, 4-Me | H | Et | Et | H | H | 58.8 | 58.7 | 6.8 | 6.8 | 6.8 | 7.3 | 83–85 |
| 137 | 3-SO₂NMe₂, 4-Me | H | Et | allyl | H | H | 60.0 | 56.7 | 6.4 | 6.4 | 6.6 | 6.3 | 420/420 |
| 138 | 4-F | H | Et | allyl | H | H | 68.1 | 69.1 | 6.3 | 6.6 | 4.4 | 4.7 | 317/317 |
| 139 | 4-F | H | Et | Et | H | H | 66.9 | 67.5 | 6.5 | 6.8 | 4.6 | 4.8 | 305/305 |
| 140 | 4-F | H | nPr | allyl | H | H | 68.8 | 69.4 | 6.6 | 7.0 | 4.2 | 4.7 | 331/331 |
| 141 | 4-F | H | nPr | Et | H | H | 67.7 | 67.6 | 6.9 | 7.2 | 4.4 | 4.4 | 319/319 |
| 142 | 4-F | H | Et | CH₂CH=CHCl cis/trans | H | H | 61.4 | 61.3 | 5.4 | 5.9 | 3.9 | 4.6 | 351/351 |
| 143 | 3-CF₃ | H | nPr | CH₂CH=CHCl cis/trans | H | H | 57.7 | 57.3 | 5.0 | 5.0 | 3.4 | 3.4 | 415/415 |
| 144 | 4-Me | H | Et | CH₂CH=CHCl cis/trans | H | H | 65.6 | 63.5 | 6.3 | 6.4 | 4.0 | 4.0 | 347/347 |
| 145 | 4-F | —SO₂—C₆H₄—Me | Et | Et | H | H | 62.7 | 61.6 | 5.6 | 6.3 | 3.0 | 2.7 | 459/459 |
| 146 | 3,4-methylenedioxy | H | nPr | Et | H | H | 66.0 | 66.0 | 6.7 | 6.5 | 4.1 | 4.2 | 72–73 |
| 147 | 3,4-di-MeO | H | Et | —CH₂—cyclopropyl | H | H | 67.6 | 67.9 | 7.2 | 7.6 | 3.8 | 4.3 | 373/373 |
| 148 | 3,4-di-MeO | H | Et | Et | H | H | 65.7 | 65.5 | 7.2 | 7.2 | 4.0 | 4.2 | 347/347 |
| 149 | 3,4-di-MeO | H | Et | allyl | H | H | 66.9 | 67.9 | 7.0 | 6.3 | 3.9 | 3.7 | 359/359 |
| 150 | 3,4-di-MeO | H | nPr | Et | H | H | 66.5 | 65.9 | 7.5 | 7.4 | 3.9 | 3.7 | 361/361 |
| 151 | 3,4-di-MeO | H | nPr | allyl | H | H | 67.6 | 66.9 | 7.2 | 7.4 | 3.8 | 3.8 | 373/373 |
| 152 | 3-CF₃ | H | nPr | —CH₂CO₂Et | H | H | 59.0 | 58.9 | 5.6 | 5.7 | 3.3 | 2.4 | 427/427 |
| 153 | 4-F | H | Et | CH₂CH=CHCl trans | H | H | 61.4 | 60.4 | 5.4 | 5.1 | 4.0 | 4.2 | 351/351 |
| 154 | 2-MeO | H | Et | CH₂CH=CHCl trans | H | H | 62.8 | 58.8 | 6.1 | 5.8 | 3.8 | 3.7 | 363/363 |
| 155 | 4-F | H | Et | —CHCH=CH₂ \| Me | H | H | 68.9 | 69.0 | 6.6 | 7.1 | 4.2 | 4.6 | 331/331 |
| 156 | 4-F | —C(=O)CH₃ | Et | allyl | H | H | 66.8 | 64.7 | 6.1 | 5.9 | 3.9 | 4.0 | 359/359 |
| 157 | 3-MeO | H | Et | allyl | H | H | 69.3 | 68.6 | 6.9 | 6.8 | 4.3 | 4.4 | 329/329 |
| 158 | 3-MeO | H | Et | Et | H | H | 68.1 | 67.2 | 7.2 | 7.0 | 4.4 | 4.7 | 317/317 |
| 159 | 3-MeO | H | Me | Et | H | H | 67.3 | 67.2 | 6.9 | 7.1 | 4.6 | 5.2 | 303/303 |
| 160 | 3,4-methylenedioxy | H | Et | Et | H | H | 65.2 | 63.2 | 6.3 | 6.2 | 4.3 | 4.3 | 331/331 |

TABLE III-continued

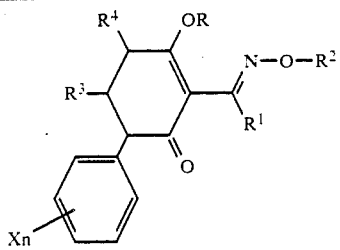

(I)

| Example No. | Xn | R | R¹ | R² | R³ | R⁴ | C Calc. % | C Fd. % | H Calc. % | H Fd. % | N Calc. % | N Fd. % | M/e (Calc/found) or mp(°C.) |
|---|---|---|---|---|---|---|---|---|---|---|---|---|---|
| 161 | 3,4-methylenedioxy | H | $^n$Pr | allyl | H | H | 67.2 | 67.6 | 6.5 | 6.5 | 3.9 | 4.3 | 357/357 |
| 162 | 3,4-methylenedioxy | H | Et | allyl | H | H | 66.5 | 66.5 | 6.1 | 6.1 | 4.1 | 3.9 | 343/343 |
| 163 | 3,4-methylenedioxy | H | Me | CH₂CH=CHCl trans | H | H | 59.4 | 59.4 | 5.0 | 5.3 | 3.9 | 4.3 | 363/363 |
| 164 | 3,4-methylenedioxy | H | Me | allyl | H | H | 65.6 | 66.4 | 5.7 | 6.0 | 4.3 | 4.6 | 329/329 |
| 165 | 4-SO₂NMe₂ | H | Et | Et | H | H | 57.8 | 57.1 | 6.6 | 6.5 | 7.1 | 7.1 | 84–85 |
| 166 | 4-F | H | $^n$Pr | —CHCH=CH₂ \| Me | H | H | 69.5 | 69.3 | 7.0 | 7.0 | 4.0 | 3.4 | 345/345 |
| 167 | 2-MeO | Me |  | Et | allyl | H | H | 70.0 | 68.6 | 7.9 | 7.9 | 4.1 | 3.7 | 343/343 |
| 168 | 2-MeO | H | $^n$Pr | Et | H | H | 68.9 | 68.3 | 7.6 | 7.6 | 4.2 | 4.4 | 331/331 |
| 169 | 4-F | H | Me | allyl | H | H | 67.3 | 66.2 | 5.9 | 6.1 | 4.6 | 4.7 | 303/303 |
| 170 | 3-$^i$PrO | H | Et | allyl | H | H | 70.6 | 69.3 | 7.6 | 7.4 | 3.9 | 4.4 | 357/357 |
| 171 | 3-$^i$PrO | H | Et | —CH₂—C≡CH | H | H | 71.0 | 71.0 | 7.0 | 7.0 | 3.9 | 4.1 | 355/355 |
| 172 | 4-F | H | Me | —CH₂—C≡CH | H | H | 67.7 | 67.5 | 5.3 | 5.5 | 4.6 | 4.8 | 301/301 |
| 173 | 4-F | H | Et | CH₂CH=CHCl cis | H | H | 61.5 | 61.4 | 5.4 | 5.4 | 4.0 | 4.2 | 351/351 |
| 174 | 3-Cl | H | Et | allyl | H | H | 64.9 | 64.9 | 6.0 | 6.0 | 4.2 | 4.2 | 333/333 |
| 175 | 3-Me | H | Et | allyl | H | H | 72.8 | 72.9 | 7.3 | 7.4 | 4.5 | 4.9 | 313/313 |
| 176 | 3-H₂C=CH—CH₂—O | H | Et | allyl | H | H | 71.0 | 71.0 | 7.0 | 7.1 | 4.0 | 4.6 | 355/355 |
| 177 | 4-F | H | Et | —CH₂CH=CH—CH₂Cl trans | H | H | 62.5 | 65.4 | 5.6 | 5.8 | 3.8 | 3.9 | 365/365 |
| 178 | 4-F | H | Et | —CH₂—C=CH₂ \| Me | H | H | 68.9 | 68.8 | 6.6 | 6.9 | 4.2 | 4.4 | 331/331 |
| 179 | 2-F | H | Et | Et | H | H | 66.9 | 66.6 | 6.6 | 6.9 | 4.6 | 4.8 | 38–41 |
| 180 | 2-F | H | Et | allyl | H | H | 68.1 | 67.8 | 6.3 | 6.5 | 4.4 | 4.6 | 317/317 |
| 181 | 3-EtO | H | Et | allyl | H | H | 70.0 | 68.4 | 7.3 | 7.4 | 4.1 | 4.1 | 343/343 |
| 182 | 3-EtO | H | Et | Et | H | H | 68.9 | 68.1 | 7.6 | 7.6 | 4.2 | 4.3 | 331/331 |
| 183 | 3-$^n$PrO | H | Et | allyl | H | H | 70.6 | 69.7 | 7.6 | 7.6 | 3.9 | 4.1 | 357/357 |
| 184 | 3-$^n$BuO | H | Et | allyl | H | H | 71.2 | 71.1 | 7.8 | 8.1 | 3.8 | 4.2 | 371/371 |
| 185 | 3-OH | H | Et | allyl | H | H | 68.6 | 64.3 | 6.7 | 6.6 | 4.4 | 4.7 | 315/315 |
| 186 | 4-CN | H | Et | allyl | H | H | 70.4 | 70.4 | 6.2 | 6.2 | 8.6 | 8.7 | 67–68 |
| 187 | H | H | Ph | allyl | H | H | 76.0 | 75.0 | 6.0 | 5.9 | 4.0 | 4.1 | 53–57 |
| 188 | 3-nPrO | H | nPr | allyl | H | H | 71.2 | 69.2 | 7.8 | 7.8 | 3.8 | 4.2 | 371/371 |
| 189 | 3-nPrO | H | nPr | Et | H | H | 70.2 | 68.4 | 8.1 | 7.6 | 3.9 | 3.9 | 359/359 |

EXAMPLE 190

Preparation of 2-[1-(allyloxyimino)-n-butyl]-3-benzoyloxy-4-(4-methoxyphenyl)-cyclohex-2-en-1-one Aqueous 1% sodium hydroxide (14 ml) was added to a stirred solution of 2-[1-(allyloxyimino)-n-butyl]-3-hydroxy-4-(4-methoxyphenyl)-cyclohex-2-en-1-one (1.2 g) in acetone (150 ml). The mixture was stirred at ambient temperature for 5 minutes and then benzoyl choloride (0.5 g) was added dropwise. After 30 minutes, the mixture was evaporated in vacuo and the residue purified on a silica gel column using 10% v/v diethyl ether-methylene chloride as eluant to give the title compound (1 g) as a colourless oil.

Mass spectometry: m/e found 447; calculated 447.
Theory for $C_{27}H_{29}NO_5$: C 72.5; H 6.5; N 3.1%.
Found: C 71.3; H 6.5; N 3.0%.

EXAMPLE 191

Preparation of sodium salt of 2-[1(ethoxyimino)-n-butyl]-3-hydroxy-4-(4-methoxyphenyl)cyclohex-2-en-1-one 2-[1-Ethoxyimino)-n-butyl]-3-hydroxy-4-(4-methoxyphenyl)cyclohex-2-en-1-one (1.3 g) was added to a solution of sodium hydroxide (0.16 g) in ethanol (20 ml) at ambient temperature. After stirring for 30 minutes, the ethanol was evaporated and the residue triturated with diethyl ether to give the title compound as a white solid (1.1 g, 79%) of m.p. 190°-191° C.

Theory for $C_{19}H_{24}O_4N$ Na: C 64.6; H 6.8; N 4.0%. Found: C 62.0; H 6.5; N 4.1%.

EXAMPLE 192

Preparation of Tetra-n-butylammonium salt of 2-[-1-(allyloxyimino)-propyl]-3-hydroxy-4-(4-fluorophenyl)-cyclohex-2-ene-1-one 2-[1-(allyloxyimino)-propyl]-3-hydroxy-4-(4-fluorophenyl)-cyclohex-2-ene-1-one (1 g) in methanol (10 ml) was added to a 25% solution of tetra-n-butylammonium hydoxide (10 ml). After standing at room temperature overnight, the methanol was evaporated in vacuo. Methylene chloride was added to the residue which was washed with water, dried over magnesium sulphate, filtered and evaporated to give the title compound as a colourless oil (0.8 g).

Theory for $C_{34}H_{54}N_2O_3F$: C 73.1; H 9.8; N 5.0%. Found: C 68.5; H 9.7; N 4.8%.

EXAMPLE 193

Preparation of Copper salt of 2-[1-(allyloxyimino)-propyl]-3-hydroxy-4-(4-fluorophenyl)-cyclohex-2-ene-1-one 2-[1-(allyloxyimino)-propyl]-3-hydroxy-4-(4-fluorophenyl)-cyclohex-2-ene-1-one (1 g) in diethyl ether (50 ml) was shaken with a saturated solution of copper (II) acetate (100 ml). The ether layer was separated and evaporated. The residual solid was washed with water and a small quantity of ether to give the title compound (0.8 g) as a pale green solid of m.p. 153–154.

Theory for $c_{36}H_{38}N_2O_6F_2Cu$: C 62.1; H 5.5; N 4.0%. Found: C 61.9; H 5.8; N 4.3%.

HERBICIDAL ACTIVITY

To evaluate their herbicidal activity, compounds according to the invention were tested using a representative range of plants: maize, *Zea mays* (Mz); rice, *Oryza sative* (R); barnyard grass, *Echinochloa crusgalli* (BG); oat, *Avena sativa* (O); linseed, *Linum usitatissimum* (L); mustard, *Sinapsis alba* (M); sugar beet, *Beta valgaris* (SB) and soya bean, *Glycine max* (S).

The tests fall into two categories, pre-emergence and post-emergence. The pre-emergence tests invloved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The fomulations used in the tests were prepared from solutions of the test compounds in acetone containing 0.4% by weight of an alkylphenol/ethylene oxide condensate available under the trade mark TRITON X-155. These acetone solutions were deluted with water and the resulting formulations applied at dosage levels corresponding to 5 kg or 1 kg of active material per hectare in a volume equivalent to 900 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale, a rating 0 indicating growth as untreated control, and a rating 9 indicating death. An increase of 1 unit on the linear scale approximates to a 10% increase in the level of effect.

The results of the tests are set out in Table IV below, in which the compounds are identified by reference to the preceding examples. The symbol * in Table IV below indicates that testing was not effected, for example because there was insufficient compound for all tests. A blank space in Table IV below corresponds to a rating 0.

TABLE IV

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 84 | | 5 | 7 | 7 | 7 | 1 | | | 5 | 5 | 7 | 8 | 5 | | | 1 | | 4 | 7 | 8 | 8 | | | 2 | |
| | | | | | | | | | 1 | 3 | 6 | 7 | 4 | | | | | 1 | | 5 | 4 | | | | |
| 85 | 6 | 7 | 7 | 7 | 1 | | | | 5 | 7 | 7 | 8 | 7 | | | | | 4 | 6 | 8 | 8 | | * 4 | 2 | |
| | | | | | | | | | 1 | 2 | 4 | 7 | 6 | | | | | 1 | 1 | 4 | 5 | | | | |
| 86 | 2 | 7 | 8 | 5 | | | | | 5 | 2 | 6 | 9 | 7 | | | | | 2 | 6 | 9 | 7 | | | 2 | |
| | | | | | | | | | 1 | 2 | 5 | 9 | 6 | | | | | | | 2 | 8 | 4 | | | |
| 87 | 6 | 5 | 8 | 6 | | | | | 5 | 7 | 7 | 9 | 7 | | | | | 4 | 6 | 9 | 7 | | 4 | 3 | |
| | | | | | | | | | 1 | 2 | 2 | 8 | 6 | | | | | 2 | 1 | 7 | 6 | | 3 | | |
| 88 | 6 | 8 | 9 | 7 | | 4 | 1 | | 5 | 8 | 9 | 9 | 8 | | | | | 8 | 9 | 9 | 8 | | 4 | 4 | |
| | | | | | | | | | 1 | 6 | 7 | 8 | 8 | | | | | 3 | 8 | 8 | 7 | | | | |
| 89 | 5 | 7 | 9 | 7 | | 2 | 3 | | 5 | 4 | 8 | 9 | 4 | | 5 | | 7 | 6 | 9 | 9 | 7 | | | | |
| | | | | | | | | | 1 | 2 | 4 | 8 | | | | | 1 | 2 | 7 | 8 | 5 | | | | |
| 90 | 7 | 4 | 8 | 7 | | 3 | 4 | | 5 | 7 | 6 | 9 | 9 | | 4 | 4 | | 6 | 9 | 9 | 8 | | 3 | 1 | |
| | | | | | | | | | 1 | 4 | 4 | 9 | 8 | | 1 | | | 2 | 4 | 9 | 6 | | 1 | 1 | |
| 91 | 7 | 4 | 8 | 6 | | 2 | 2 | | 5 | 6 | 3 | 9 | 6 | | | | | 6 | 8 | 9 | 6 | | 2 | | |
| | | | | | | | | | 1 | 2 | 2 | 8 | 2 | | | | | | 5 | 8 | 4 | | | | |
| 92 | 5 | 6 | 7 | 7 | | | | | 5 | 7 | 5 | 8 | 8 | 2 | 3 | 3 | 1 | 6 | 8 | 8 | 7 | | | | |
| | | | | | | | | | 1 | 3 | 2 | 7 | 7 | | | | | 2 | 6 | 4 | 6 | | | | |
| 98 | 1 | 2 | 5 | 2 | 1 | 3 | 2 | | 5 | 7 | 5 | 8 | * 6 | | 4 | 4 | 3 | 2 | 4 | 3 | | | | | |
| | | | | | | | | | 1 | 3 | 1 | 7 | 1 | | 1 | 1 | | | | | | | | | |
| 83 | 4 | 7 | 8 | 6 | | | | | 5 | 5 | 6 | 8 | 7 | | | | | 5 | 8 | 9 | 6 | | | | |

TABLE IV-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 82 | 5 | 7 | 9 | 7 | | | | | 5 | 2 | 4 | 7 | 2 | | | | | | 4 | 8 | 4 | | | | |
| | | | | | | | | | 1 | 7 | 7 | 8 | 8 | | | | | 4 | 8 | 9 | 6 | | | | |
| 81 | 4 | 7 | 7 | 8 | | | | | 5 | 3 | 3 | 7 | 8 | | | | | 1 | 3 | 7 | 5 | | | | |
| | | | | | | | | | 1 | 8 | 8 | 8 | 8 | | | | | 5 | 9 | 9 | 6 | | 2 | | |
| 80 | 6 | 8 | 9 | 8 | | | | | 5 | 5 | 5 | 7 | | | | | | | 4 | 5 | 4 | | 1 | | |
| | | | | | | | | | 1 | 8 | 8 | 9 | 8 | | | | | 6 | 9 | 9 | 7 | | | | |
| 93 | 2 | 7 | 8 | 3 | 2 | | | | 5 | 5 | 5 | 8 | 8 | | | | | 3 | 7 | 8 | 6 | | | | |
| | | | | | | | | | 1 | 1 | 4 | 8 | | | 5 | | 3 | 3 | 7 | 9 | 7 | | | 3 | |
| 94 | 5 | 7 | 8 | 6 | 2 | | | | 5 | | 1 | 7 | | | 2 | | | | 3 | 5 | 3 | | | 2 | |
| | | | | | | | | | 1 | 5 | 5 | 8 | 6 | | 4 | 1 | | 5 | 8 | 8 | 8 | | | | |
| 95 | 6 | 8 | 9 | 7 | 4 | 5 | 5 | 3 | 5 | 3 | 1 | 8 | 4 | | | | | 2 | 5 | 4 | 5 | | | | |
| | | | | | | | | | 1 | 4 | 6 | 8 | 4 | | 5 | 4 | 1 | 7 | 9 | 9 | 8 | | | 3 | |
| 96 | 5 | 8 | 9 | 9 | | 3 | 4 | 3 | 5 | 1 | 5 | 8 | 2 | | 2 | | | 2 | 7 | 7 | 7 | | | | |
| | | | | | | | | | 1 | 7 | 8 | 9 | 8 | | 6 | 3 | | 7 | 9 | 9 | 8 | | | 3 | |
| 97 | 2 | 4 | 8 | 2 | | 6 | 5 | | 5 | 4 | 7 | 8 | 8 | | 2 | | | | 7 | 6 | 7 | | | | |
| | | | | | | | | | 1 | 2 | 3 | 7 | 2 | | 5 | | | 3 | 7 | 9 | 7 | | | 4 | |
| 190 | 6 | 8 | 9 | 9 | | | | | 5 | 1 | 1 | 7 | | | 1 | | | | 2 | 5 | 4 | | | | |
| | | | | | | | | | 1 | 2 | 3 | 8 | 7 | | 4 | 2 | | 2 | 8 | 8 | 6 | | | | |
| 79 | 6 | 8 | 9 | 9 | | | | | 5 | 2 | | 6 | 3 | | 3 | | | | 5 | 3 | 3 | | | | |
| | | | | | | | | | 1 | 7 | 8 | 9 | 9 | | | | | 7 | 9 | 9 | 8 | | | | |
| 99 | 6 | 8 | 9 | 9 | | | | | 5 | 5 | 5 | 8 | 8 | | | | | 2 | 7 | 7 | 7 | | | | |
| | | | | | | | | | 1 | 5 | 7 | 8 | 8 | | | | | 6 | 9 | 9 | 7 | | | 2 | |
| 191 | 4 | 7 | 8 | 8 | | | | | 5 | 3 | 6 | 8 | 8 | | | | | 2 | 7 | 7 | 6 | | | | |
| | | | | | | | | | 1 | 2 | 7 | 8 | 5 | | 2 | 2 | | 5 | 9 | 9 | 7 | | | | |
| 100 | 7 | 8 | 8 | | | | | 5 | 5 | 1 | 4 | 7 | 2 | | | | | | 4 | 4 | 5 | | | | |
| | | | | | | | | | 1 | 6 | 9 | 7 | | | 2 | | 7 | 7 | 9 | 7 | | | | | |
| 101 | 6 | 7 | 9 | 7 | | 3 | 4 | | 5 | 1 | 2 | 8 | 3 | | | | | | 3 | 4 | 4 | | | | |
| | | | | | | | | | 1 | 4 | 4 | 9 | | | | 2 | | 7 | 7 | 9 | 6 | | 1 | 2 | |
| 135 | 2 | 5 | 6 | 3 | | | | | 5 | 2 | 2 | 8 | | | | | | 0 | 1 | 7 | 3 | | | | |
| | | | | | | | | | 1 | 4 | 4 | 7 | 7 | 1 | | | 2 | 3 | 3 | 8 | 7 | | | | |
| 111 | | 1 | 4 | | | | | 3 | 5 | 2 | | 5 | | | | | | | 2 | 4 | 2 | | | | |
| | | | | | | | | | 1 | | | 7 | | | 3 | | | | | | | | | | |
| 113 | | 2 | 4 | | 3 | | 2 | 2 | 5 | | | 3 | | | | | | | | | | | | | |
| | | | | | | | | | 1 | | | 8 | | | 2 | | 2 | | | 4 | | | | | |
| 114 | | 1 | 2 | | | | | | 5 | | | 4 | | | | | | | | 3 | | | | | |
| | | | | | | | | | 1 | | | 6 | | | 1 | | | | | | | | | | |
| 122 | 5 | 6 | 7 | 5 | 3 | 4 | | 3 | 5 | | | 2 | | | | | | | | | | | | | |
| | | | | | | | | | 1 | 4 | 7 | 7 | 7 | | 4 | 2 | | | | | | | | | |
| 167 | 4 | 3 | 7 | 4 | | | | | 5 | 3 | 5 | 6 | | | | | | | | 7 | 4 | | | | |
| | | | | | | | | | 1 | 2 | 1 | 5 | 4 | 3 | 3 | | 1 | | | | | | | | |
| 168 | 4 | 5 | 7 | 2 | | | | | 5 | 1 | | 3 | | | | | | | | 5 | | | | | |
| | | | | | | | | | 1 | 4 | 4 | 8 | 3 | 2 | 2 | | | 2 | * | * | 5 | | | | |
| 123 | 6 | 6 | 9 | 6 | | | | | 5 | 3 | 3 | 7 | 1 | | | | | | | * | 9 | 7 | | | | |
| | | | | | | | | | 1 | 7 | 7 | 9 | 7 | | 1 | | 1 | 5 | * | 8 | 5 | | | | |
| 124 | | | | | | | | | 5 | 6 | 6 | 7 | 7 | | | | | | | | | | | | |
| | | | | | | | | | 1 | 2 | 2 | 5 | 1 | 4 | 3 | | 3 | 3 | 5 | 4 | 4 | 3 | | | |
| 125 | 2 | 1 | 5 | 3 | 5 | 2 | | | 5 | 1 | | 5 | | 2 | | | | | | 1 | 1 | | | | |
| | | | | | | | | | 1 | 5 | 4 | 6 | 3 | 4 | 4 | 3 | 4 | 2 | 3 | 7 | 7 | 2 | | 2 | |
| 126 | 2 | 2 | 6 | 2 | 6 | 6 | | | 5 | 3 | 2 | 4 | 1 | | | | | | | 1 | 5 | | | | |
| | | | | | | | | | 1 | 3 | 3 | 6 | 2 | 6 | 3 | | 2 | 2 | * | 7 | 6 | 4 | 3 | 2 | |
| 127 | 3 | 3 | 6 | 3 | 6 | 2 | | | 5 | 1 | 1 | 5 | 1 | 3 | | | | | | 2 | | | 1 | 1 | |
| | | | | | | | | | 1 | 4 | 5 | 8 | 6 | 6 | 5 | 3 | 3 | 3 | * | 8 | 7 | 4 | 2 | | |
| 129 | 4 | 4 | 9 | 7 | 2 | 2 | | | 5 | 2 | 3 | 6 | 1 | 1 | | 1 | | | | 4 | 2 | | | | |
| | | | | | | | | | 1 | 4 | 2 | 7 | 2 | | | | | | | 7 | 2 | | | | |
| 131 | | | 2 | | | | | | 5 | 2 | | 3 | | | | | | | | | | | | | |
| | | | | | | | | | 1 | 4 | 3 | 6 | | | 3 | 2 | | | | 6 | | | | | |
| 132 | | | | | | | | | 5 | 2 | | 6 | | | | | | | | | | | | | |
| | | | | | | | | | 1 | 3 | 1 | 2 | 1 | 4 | 4 | | 1 | | | | | | | | |
| 133 | | | | | | | | | 5 | 2 | | | | | 2 | 1 | | | | | | | | | |
| | | | | | | | | | 1 | 3 | | 4 | 1 | 1 | 5 | 2 | | | | 5 | | | | | |
| 134 | | | 4 | | | | | | 5 | 1 | | | | | 4 | | | | | | | | | | |
| | | | | | | | | | 1 | 3 | | 4 | | | | | | | | 7 | | | | | |
| 147 | 2 | 4 | 7 | 4 | | | 2 | | 5 | 1 | | 2 | | | | | | | | | | | | | |
| | | | | | | | | | 1 | 3 | 3 | 7 | 1 | | | | | 3 | 3 | 8 | 3 | | | | |
| 148 | 6 | 8 | 9 | 8 | 3 | 3 | 3 | | 5 | 2 | 1 | 5 | 1 | | | | | | | 3 | | | | | |
| | | | | | | | | | 1 | 6 | 7 | 9 | 7 | | 4 | 3 | 2 | 3 | 8 | 9 | 7 | | | | |
| 149 | 5 | 7 | 9 | | 8 | 2 | 2 | 2 | 5 | 4 | 6 | 8 | 7 | | | | 2 | | * | 9 | 5 | | | | |
| | | | | | | | | | 1 | 5 | 5 | 7 | 9 | 8 | | | 2 | | 9 | 9 | 8 | | | | |
| 150 | 4 | 7 | 7 | 7 | 2 | 3 | | 2 | 5 | 4 | 6 | 7 | 7 | | | | | | * | 9 | 6 | | | | |
| | | | | | | | | | 1 | 6 | 6 | 7 | 7 | | | | 2 | 5 | 8 | 9 | 6 | | | | |
| 151 | 5 | 7 | 7 | 7 | 2 | 1 | | | 5 | 5 | 5 | 6 | 7 | | | | | 4 | 2 | 5 | | | | | |
| | | | | | | | | | 1 | 7 | 7 | 9 | 8 | | | | 1 | | | | | | | | |
| 115 | | 7 | 4 | 3 | | | | | 5 | 3 | 6 | 7 | 7 | | | | | | * | 6 | 7 | | | | |
| | | | | | | | | | 1 | 4 | 6 | 7 | 4 | | | | | | | | | | | | |
| 116 | 4 | 6 | 7 | 3 | | | | | 5 | 3 | 1 | 6 | 1 | | | | | 2 | 8 | 8 | 5 | | 2 | | |
| | | | | | | | | | 1 | 7 | 7 | 8 | 5 | 1 | 2 | | | | | 3 | | | 1 | | |
| 117 | 4 | 7 | 7 | 5 | 2 | | 3 | | 5 | 4 | 1 | 7 | 2 | | | | | 5 | 8 | 9 | 6 | | 4 | | |
| | | | | | | | | | 1 | 6 | 7 | 9 | 5 | 1 | 2 | | | | | | | | | | |

TABLE IV-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 118 | 3 | 6 | 8 | 7 | | | | | 1 | 3 | 2 | 7 | | | | | | 2 | * | 5 | | | 2 | | |
| | | | | | | | | | 5 | 2 | 7 | 9 | 8 | | 3 | | 2 | 4 | 6 | 9 | 8 | | | | |
| 119 | 4 | 8 | 8 | 7 | | | | | 1 | | 6 | 8 | 4 | | | | | 1 | 3 | 7 | 3 | | | | |
| | | | | | | | | | 5 | 7 | 8 | 9 | 7 | | | | 1 | 6 | 8 | 9 | 8 | | 3 | | |
| 120 | 4 | 7 | 8 | 5 | | | | | 1 | | | | | | | | | 1 | 3 | 8 | 4 | | | | |
| | | | | | | | | | 5 | 7 | 8 | 9 | 7 | | 1 | 3 | 2 | 5 | 7 | 9 | 8 | | 2 | 2 | |
| 121 | 3 | 4 | 6 | 6 | | | | | 1 | 3 | 5 | 8 | 4 | | | 1 | | 1 | 4 | 8 | 5 | | | | |
| | | | | | | | | | 5 | 6 | 7 | 8 | 6 | | | 2 | 1 | 3 | 6 | 9 | 8 | | | | |
| 137 | 9 | 7 | 8 | 8 | | | | | 1 | 4 | 2 | 7 | 3 | | | | | 1 | 2 | 6 | 5 | | | | |
| | | | | | | | | | 5 | 8 | 7 | 8 | 7 | | | | | 2 | 3 | 9 | 8 | | | | |
| 136 | 8 | 8 | 8 | 9 | 2 | 7 | 3 | | 1 | 3 | 4 | 6 | 3 | | | | | | | 7 | 5 | | | | |
| | | | | | | | | | 5 | 5 | 7 | 9 | 8 | | 5 | | | 7 | 8 | 9 | 9 | | 3 | | |
| 138 | 8 | 9 | 9 | 9 | | 4 | 2 | | 1 | 3 | 6 | 7 | 4 | | 2 | | | 2 | | 7 | 7 | | | | |
| | | | | | | | | | 5 | 7 | 8 | 9 | 9 | | 6 | 6 | 3 | 7 | 9 | 9 | 8 | | 2 | 5 | 4 |
| 139 | 7 | 9 | 9 | 8 | | 3 | 2 | | 1 | 4 | 8 | 9 | 7 | | | 2 | | 4 | 8 | 9 | 6 | | 2 | 2 | 2 |
| | | | | | | | | | 5 | 5 | 8 | 8 | 5 | 2 | 5 | 4 | 2 | 7 | 9 | 9 | 6 | | 2 | 3 | 3 |
| 140 | 6 | 9 | 9 | 8 | | | 2 | | 1 | 3 | 7 | 8 | 2 | | | 1 | | 5 | 8 | 9 | 5 | | | 1 | |
| | | | | | | | | | 5 | 8 | 8 | 9 | 9 | | 6 | 3 | 2 | 7 | 9 | 9 | 8 | | 2 | 3 | 1 |
| 141 | 3 | 7 | 8 | 7 | | 2 | 2 | 1 | 1 | 7 | 7 | 9 | 7 | | | | | 4 | 7 | 8 | 5 | | | 1 | |
| | | | | | | | | | 5 | 4 | 7 | 9 | 4 | 3 | 6 | 3 | 2 | 6 | 9 | 9 | 6 | | 1 | 2 | 5 |
| 142 | 7 | 7 | 8 | 3 | | | | | 1 | 2 | 7 | 8 | 1 | | | | | 2 | 7 | 8 | 5 | | | 1 | |
| | | | | | | | | | 5 | 6 | 6 | 8 | 1 | | 3 | 1 | 3 | 4 | 8 | 8 | 3 | | | | |
| 144 | 5 | 7 | 6 | 2 | | | | | 1 | 4 | 4 | 8 | | | | | | 1 | 5 | 5 | | | | | |
| | | | | | | | | | 5 | 6 | 6 | 8 | | | | | | 6 | 8 | 7 | 6 | | | | |
| 145 | | 5 | 6 | | | | | | 1 | 3 | 5 | 7 | | | | | | | 3 | 6 | | | | | |
| | | | | | | | | | 5 | 2 | 4 | 7 | | | | | 1 | | 4 | 6 | | | | | |
| 146 | 8 | 8 | 8 | 8 | | | | | 1 | | 2 | 5 | | | | | | | | | | | | | |
| | | | | | | | | | 5 | 9 | 9 | 9 | 8 | 3 | 8 | 6 | | 7 | 8 | 9 | 8 | | 2 | 4 | 3 |
| 157 | 2 | 8 | 9 | 8 | | | | 2 | 1 | 7 | 8 | 9 | 8 | | 2 | 2 | | 6 | 6 | 8 | 6 | | | | |
| | | | | | | | | | 5 | 6 | 8 | 9 | 9 | | 2 | 3 | | 6 | 7 | 9 | 7 | | | | |
| 158 | | 8 | 8 | 7 | | | | | 1 | 4 | 7 | 9 | 7 | | | 1 | | | 4 | 8 | 4 | | | | |
| | | | | | | | | | 5 | 4 | 8 | 9 | 6 | 3 | 2 | | 4 | 8 | 9 | 7 | | | | | |
| 159 | | 8 | 8 | | | | | | 1 | 1 | 7 | 9 | | | | | | | 3 | 7 | 2 | | | | |
| | | | | | | | | | 5 | 4 | 7 | 9 | | | | | | 4 | 8 | 8 | | | | | |
| 160 | 7 | 8 | 9 | 8 | 3 | 4 | 5 | 2 | 1 | 1 | 4 | 8 | | | | | | | 3 | 7 | | | | | |
| | | | | | | | | | 5 | 7 | 8 | 9 | 9 | 3 | 6 | 5 | 2 | 7 | 9 | 9 | 8 | | 3 | | |
| 161 | 7 | 8 | 9 | 8 | | | 3 | | 1 | 6 | 7 | 9 | 8 | | 4 | 3 | | 3 | 6 | 8 | 6 | | | | |
| | | | | | | | | | 5 | 8 | 8 | 9 | 8 | 2 | 5 | 5 | | 6 | 9 | 9 | 8 | | | | |
| 162 | 6 | 8 | 9 | 8 | | 2 | 4 | | 1 | 6 | 4 | 9 | 7 | 1 | 1 | | | 3 | 7 | 7 | 6 | | | | |
| | | | | | | | | | 5 | 9 | 8 | 9 | 8 | 3 | 5 | 5 | | 7 | 9 | 9 | 8 | | | | |
| 153 | 5 | 7 | 7 | 7 | | | | | 1 | 5 | 7 | 9 | 7 | | 1 | 1 | | 4 | 8 | 8 | 6 | | | | |
| | | | | | | | | | 5 | 6 | 7 | 8 | 6 | | 2 | | 2 | 6 | 9 | 9 | 7 | | | | |
| 154 | 6 | 6 | 8 | | | | | | 1 | 5 | 6 | 8 | 4 | | | | | 1 | 8 | 8 | 4 | | | | |
| | | | | | | | | | 5 | 4 | 3 | 8 | 3 | | 3 | 4 | | 4 | 7 | 8 | 5 | | | | |
| 155 | | 3 | 3 | 2 | | | | | 1 | 2 | | 8 | 1 | | | 1 | | 1 | 5 | 3 | 1 | | | | |
| | | | | | | | | | 5 | 2 | | 7 | 2 | 2 | | 3 | | 7 | 8 | 5 | | 3 | | | |
| 166 | 2 | 2 | 8 | | | | | 2 | 1 | 1 | | 6 | 2 | | | 2 | | 2 | | | | | | | |
| | | | | | | | | | 5 | 4 | 2 | 8 | 2 | 2 | 2 | 4 | 5 | 2 | 4 | 5 | 5 | | | | |
| 163 | 7 | 8 | 7 | 3 | | 2 | | | 1 | 1 | 1 | 8 | 1 | | | | | | 1 | 1 | | | | | |
| | | | | | | | | | 5 | 8 | 8 | 9 | 7 | 4 | 4 | 5 | | 2 | 6 | 8 | 2 | | | | |
| 164 | 7 | 8 | 8 | 6 | 3 | 2 | | | 1 | 7 | 7 | 8 | 5 | 2 | 3 | 2 | | 1 | 5 | 5 | | | | | |
| | | | | | | | | | 5 | 8 | 8 | 9 | 8 | 4 | 4 | 3 | | 5 | 6 | 9 | 3 | | | | |
| 165 | 7 | 8 | 8 | 9 | | | | 3 | 1 | 5 | 5 | 8 | 7 | | | 1 | | | 5 | 4 | | | | | |
| | | | | | | | | | 5 | 7 | 8 | 9 | 8 | 3 | 4 | 4 | 3 | 6 | 9 | 9 | 9 | | | | |
| 192 | 6 | 8 | 9 | 8 | 4 | | | | 1 | 4 | 6 | 7 | 7 | | 1 | | | | 5 | 5 | 6 | | | | |
| | | | | | | | | | 5 | 7 | 7 | 9 | 8 | | | 1 | 2 | 7 | 9 | 9 | 7 | | | | |
| 193 | 6 | 8 | 8 | 8 | 2 | | | | 1 | 5 | 6 | 9 | 7 | | | | 1 | 2 | 8 | 8 | 5 | | | | |
| | | | | | | | | | 5 | 6 | 8 | 9 | 7 | | | | | 6 | 8 | 9 | 7 | | | | |
| 156 | 6 | 8 | 8 | 7 | | | | | 1 | 6 | 6 | 9 | 7 | | | | | 3 | 8 | 8 | 7 | | | | |
| | | | | | | | | | 5 | 6 | 7 | 9 | 8 | | 1 | 3 | 2 | 3 | 8 | 9 | 7 | | | | |
| 169 | 4 | 7 | 9 | 5 | | | | | 1 | 6 | 6 | 9 | 6 | | | | | 1 | 8 | 8 | 6 | | | | |
| | | | | | | | | | 5 | 7 | 8 | 9 | 8 | 2 | 4 | 3 | 2 | 7 | 9 | 9 | 8 | | | | |
| 170 | 7 | 6 | 8 | 4 | | | | | 1 | 4 | 7 | 9 | 7 | 1 | | | 1 | | 7 | 8 | 7 | | | | |
| | | | | | | | | | 5 | 7 | 7 | 9 | 8 | | | 2 | | 6 | 8 | 9 | 7 | | | | |
| 173 | 7 | 6 | 8 | | 5 | 2 | | | 1 | 5 | 6 | 9 | 8 | | | | | | 6 | 8 | 7 | | | | |
| | | | | | | | | | 5 | 5 | 5 | 9 | 4 | 2 | 4 | 2 | 2 | 8 | 9 | 9 | 7 | 4 | 4 | 2 | |
| 174 | 4 | 2 | 8 | 2 | | | | | 1 | 4 | 2 | 8 | | | | | | | 7 | 8 | 2 | | 2 | | |
| | | | | | | | | | 5 | 5 | 6 | 9 | 7 | | 5 | 4 | | 4 | 8 | 8 | 7 | | | | |
| 178 | 3 | 4 | 8 | 2 | | | | | 1 | 2 | | 7 | 6 | | | 1 | | 1 | 3 | 6 | 4 | | | | |
| | | | | | | | | | 5 | 3 | 4 | 8 | 3 | 2 | 4 | 4 | 2 | 2 | 8 | 8 | 4 | | | | |
| 179 | 2 | 3 | 8 | | 2 | | | | 1 | 1 | 2 | 8 | 2 | | | | | | 4 | 5 | 2 | | | | |
| | | | | | | | | | 5 | 3 | 2 | 9 | 3 | | 4 | 3 | 3 | 7 | 7 | 9 | 7 | | | | |
| 180 | 5 | 5 | 9 | 6 | | | | | 1 | 1 | | 8 | | | | | | | 2 | 5 | 8 | 2 | | | |
| | | | | | | | | | 5 | 7 | 8 | 9 | 9 | 1 | 4 | 4 | 2 | 7 | 8 | 9 | 8 | | | | |
| 171 | 7 | 7 | 8 | 7 | | | | | 1 | 6 | 3 | 9 | 7 | | | | | | 3 | 6 | 8 | 6 | | | |
| | | | | | | | | | 5 | 7 | 7 | 9 | 8 | | | | | 4 | 8 | 9 | 7 | | | | |
| 172 | 5 | 7 | 8 | 7 | 2 | 5 | 4 | | 1 | 3 | 2 | 9 | 7 | | | | | | 5 | 7 | 5 | | | | |
| | | | | | | | | | 5 | 8 | 8 | 9 | 8 | 1 | 5 | 4 | 3 | 7 | 9 | 9 | 8 | | | 4 | 2 |

TABLE IV-continued

| Compound of Ex. No. | Soil drench 10/kg/ha | | | | | | | | Dosage kg/ha | Foliar spray | | | | | | | | Pre-emergence | | | | | | | |
| --- | --- | --- | --- | --- | --- | --- | --- | --- | --- | --- | --- | --- | --- | --- | --- | --- | --- | --- | --- | --- | --- | --- | --- | --- |
| | Mz | R | BG | O | L | M | SB | S | | Mz | R | BG | O | L | M | SB | S | Mz | R | BG | O | L | M | SB | S |
| 176 | 7 | 8 | 8 | 7 | | | | | 1 | 5 | 6 | 8 | 7 | | | 1 | 1 | 2 | 7 | 8 | 3 | | | | |
| | | | | | | | | | 5 | 7 | 7 | 9 | 8 | | | 3 | 4 | 8 | 8 | 9 | 7 | | | | |
| | | | | | | | | | 1 | 4 | 4 | 9 | 7 | | | 2 | | | 6 | 8 | 4 | | | | |

We claim:
1. A compound of the general formula

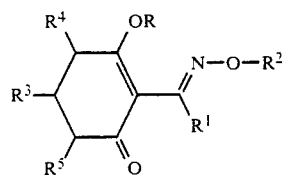

wherein
  R represents a hydrogen atom, or an optionally substituted alkyl group, or an acyl, an alkenyl or alkynyl group or an inorganic or organic cation;
  $R^1$ represents an alkyl, haloalkyl, alkenyl, alkynyl or phenyl group;
  $R^2$ represents an optionally substituted alkyl group or a phenylalkyl, cycloalkyl, alkenyl, haloakenyl, alkynyl or haloalkynyl group;
  $R^3$ represents a hydrogen atom or an alkyl group; and
  one of $R^4$ and $R^5$ represents a hydrogen atom or an alkyl group, while the other of $R^4$ and $R^5$ represents an optionally substituted phenyl group; and
  said cation being selected from the group consisting of alkali and alkaline earth metal ions, transition metal ions, and ammonium ions, said ammonium ions being optionally substituted by 1-4 groups independently selected from otpionally substituted alkyl groups, optionally substituted phenyl groups and phenylalkyl groups; and
  the optional substitution on alkyl group of R and $R^2$ and on alkyl group optionally substituted on ammonium ion being by one or more moieties independently selected from halogen atoms and $C_{1-6}$ alkoxy, $C_{1-6}$ alkylthio, ($C_{1-6}$ alkoxy)carbonyl, and optionally substituted phenyl groups; and
  the optional substitution on phenyl group of $R^4$ or $R^5$, on phenyl group optionally substituted on alkyl of R and on phenyl group optionally substituted on alkyl of $R^2$ and on phenyl group optionally substituted on ammonium ion being by one or more moieties independently selected from halogen atoms and nitro, cyano, $C_{1-6}$ alkyl, $C_{1-6}$ haloalkyl, $C_{1-6}$ alkoxy, $C_{1-6}$ alkylthio, $C_{2-6}$ alkenylthio and alkynylthio, $C_{3-6}$ cycloalkylthio, benzylthio optionally substituted by 1-3 atoms of halogen, and $C_{1-6}$ alkyl, alkoxy, alkenyloxy, alkynyloxy, and haloalkyl; and amino, acetamido, mono ($C_{1-4}$) alkylamino and di($C_{1-4}$-alkyl)amino groups, and 2. A compound as claimed in claim 1, wherein R represents a hydrogen atom, or said organic or inorganic cation, or a $C_{2-6}$ alkanoyl group, or an alkyl or arylsulphonyl group, or a benzoyl group which is optionally substituted by 1-3 substituents independently selected from halogen, nitro, $C_{1-6}$ alkyl or $C_{1-6}$ alkoxy.

3. A compound as claimed in claim 1 or 2, wherein $R^1$ represents a $C_{1-6}$ alkyl group or a phenyl group.

4. A compound as claimed in claim 1 or 2, wherein $R^2$ represents a $C_{1-6}$ alkyl group optionally substituted by one or more moieties independently selected from halogen atoms and $C_{1-6}$ alkoxy, $C_{1-6}$ alkoxycarbonyl, $C_{3-6}$ cycloalkyl and $C_{1-6}$ alkylthio groups; or a $C_{2-6}$ alkenyl, haloalkenyl, alkynyl, or haloalkynyl group or a benzyl group.

5. A compound as claimed in claim 1 or 2, wherein $R^3$ represents a hydrogen atom or a $C_{1-4}$ alkyl group.

6. A compound of the formula

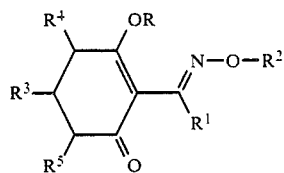

wherein
  R represents a hydrogen atom, or an organic or inorganic cation or a $C_{2-6}$ alkanoyl group, or an alkyl or arylsulphonyl group, or a benzyl group which is optionally substituted by 1-3 substituents independently selected from halogen, nitro, $C_{1-6}$ alkyl or $C_{1-6}$ alkoxy; wherein $R^1$ represents a $C_{1-6}$ alkyl group or a phenyl group; wherein $R^2$ represents a $C_{1-6}$ alkyl group optionally substituted by one or more moieties independently selected from halogen atoms and $C_{1-6}$ alkoxy, $C_{1-6}$ alkoxycarbonyl, $C_{3-6}$ cycloalkyl and $C_{1-6}$ alkylthio groups; or a $C_{2-6}$ alkenyl, haloalkenyl, alkynyl, or haloalkynyl group or a benzyl group; wherein $R^3$ represents a hydrogen atom or a $C_{1-4}$ alkyl group; and wherein one of $R^4$ or $R^5$ represents a phenyl group optionally substituted by 1-5 moieties independently selected from halogen atoms and $C_{1-6}$ alkyl, $C_{1-6}$ alkoxy, cyano, nitro, hydroxy, acyl, $C_{1-6}$ haloalkyl, $C_{2-6}$ alkenyloxy and methylenedioxy groups, while the other of $R^4$ or $R^5$ represents a hydrogen atom or a $C_{1-4}$ alkyl group, and said cation being selected from the group consisting of alkali and alkaline earth metal ions, transition metal ions, and ammonium ions, said ammonium ions being optionally substituted by 1-4 groups independently selected from optionally substituted alkyl groups, optionally substituted phenyl groups and phenylalkyl groups; and the optional substitution on alkyl group optionally substituted on ammonium ion being by one or more moieties independently selected from halogen atoms and $C_{1-6}$ alkoxy, $C_{1-6}$ alkylthio, ($C_{1-6}$ alkoxy)carbonyl, and optionally substituted phenyl groups; and the optional substitution on phenyl group optionally substituted on ammonium ion being by one or more moieties independently selected from halogen atoms and nitro, cyano, $C_{1-6}$ alkyl, $C_{1-6}$ haloalkyl, $C_{1-6}$ alkoxy, $C_{1-6}$ alkylthio, $C_{2-6}$ alkenylthio and alkynylthio, $C_{3-6}$ cycloalkylthio, benzylthio optionally substituted by 1-3 atoms of halogen, and $C_{1-6}$ alkyl, alkoxy, alkenyloxy, alkynyloxy, and haloalkyl; and amino, acetamido, mono($C_{1-4}$) alkylamino and di($C_{1-4}$-alkyl)amino groups, and acyl groups.

7. The compound of claim 1 wherein R is H, $R^1$ is ethyl, $R^2$ is allyl, $R^3$ is H and $R^5$ is phenyl substituted with F at the 4-position.

8. A herbicidal composition, comprising from 0.5% to 95% by weight of a compound of formula I, as claimed in claim 1 or 6, together with at least one carrier.

9. A method of combating undesired plant growth at a locus by treating the locus with a compound as claimed in claim 1 or 6, or a composition comprising from 0.5% to 95% by weight of said compound and at least one carrier, the dosage of said compound being from 0.1 to 10 kg/ha.

* * * * *

UNITED STATES PATENT AND TRADEMARK OFFICE
CERTIFICATE OF CORRECTION

PATENT NO. : 4,921,524

DATED : May 1, 1990

INVENTOR(S) : TERENCE GILKERSON ET AL

It is certified that error appears in the above-identified patent and that said Letters Patent is hereby corrected as shown below:

Claim 1 (column 25, line 59), after "groups, and" insert --acyl groups--.

Claim 6 (column 26, line 32), change "benzyl" to --benzoyl--.

Claim 9 (column 28, line 9), change "0.1" to --0.01--.

Signed and Sealed this

Sixteenth Day of July, 1991

Attest:

HARRY F. MANBECK, JR.

Attesting Officer

Commissioner of Patents and Trademarks